United States Patent [19]

Saab

[11] Patent Number: 5,337,734

[45] Date of Patent: Aug. 16, 1994

[54] DISPOSABLE SHEATH WITH OPTICALLY TRANSPARENT WINDOW FORMED CONTINUOUSLY INTEGRAL THEREWITH

[75] Inventor: Mark A. Saab, Lowell, Mass.

[73] Assignee: Advanced Polymers, Incorporated, Salem, N.H.

[21] Appl. No.: 968,538

[22] Filed: Oct. 29, 1992

[51] Int. Cl.$^5$ .................................................. A61B 1/00
[52] U.S. Cl. .................................................................. 128/4
[58] Field of Search .................. 128/6, 844, 917, 918, 128/4; 359/510, 511

[56] References Cited

U.S. PATENT DOCUMENTS

| Re. 32,983 | 7/1989 | Levy | 428/36.92 |
|---|---|---|---|
| Re. 33,561 | 3/1991 | Levy | 428/36.92 |
| 3,162,190 | 12/1964 | Del Gizzo | 128/6 |
| 3,794,091 | 2/1974 | Ersek et al. | 150/52 R |
| 3,809,072 | 5/1974 | Ersek et al. | 128/23 |
| 4,201,199 | 5/1980 | Smith | 128/7 |
| 4,470,407 | 9/1984 | Hussein | 128/6 |
| 4,576,156 | 3/1986 | Dyck et al. | 128/844 |
| 4,646,722 | 3/1987 | Silverstein | 128/4 |
| 4,684,490 | 8/1987 | Taller et al. | 128/844 X |
| 4,698,791 | 10/1987 | Walchle et al. | 350/61 |
| 4,741,326 | 5/1988 | Sidall et al. | 128/4 |
| 4,819,620 | 4/1989 | Okutsu | 128/4 |
| 4,820,349 | 4/1989 | Saab | 128/344 |
| 4,878,485 | 11/1989 | Adair | 128/6 |
| 4,886,049 | 12/1989 | Darras | 128/4 |
| 4,907,395 | 3/1990 | Opie et al. | 53/434 |
| 4,957,112 | 9/1990 | Yokoi et al. | 128/662.06 |
| 5,024,852 | 6/1991 | Busnel et al. | 128/844 X |
| 5,029,574 | 7/1991 | Shimamura et al. | 128/6 |
| 5,078,483 | 1/1991 | Herzberg | 359/510 |
| 5,176,152 | 1/1993 | Wheeler | 128/844 |

*Primary Examiner*—Richard J. Apley
*Assistant Examiner*—Beverly A. Meindl
*Attorney, Agent, or Firm*—Lappin & Kusmer

[57] ABSTRACT

Sterile disposable coverings for endoscopes and similar optical medical instruments are disclosed together with a method for preparing such coverings. By forming a heated polymeric film with a mandrel of appropriate shape and dimensions, relatively long-length, very small diameter, closely-fitting, thin-walled sleeves are produced, each having a thin, substantially inelastic, optically transparent window formed continuously integral with the sleeve at or proximate to the closed, distal end of the sleeve.

66 Claims, 3 Drawing Sheets under the structure
DISPOSABLE SHEATH WITH OPTICALLY TRANSPARENT WINDOW FORMED CONTINUOUSLY INTEGRAL THEREWITH The present invention relates generally to sterile, disposable sheaths or coverings for endoscopes and similar medical instruments, and, more particularly, to very thin-walled, relatively inelastic sleeves each having a very thin, relatively inelastic, optically transparent window formed continuously integral with the sleeve at or proximate to the closed, distal end of the sleeve.

BACKGROUND OF THE INVENTION

The use of endoscopes and similar medical instruments for diagnostic and therapeutic applications is well known in the art. Such devices are used for viewing virtually anywhere within the body. To eliminate the problems of cleaning and sterilizing these instruments between uses, it is known to cover these devices during use with sealed, protective sheaths, sleeves and covers of various sorts. Such sheaths are commonly elongated, tubular sleeves each having one open end for inserting the medical instruments and one closed, distal end. After use, the protective sheath is removed from the instrument and discarded. Thus, the cost of the protective sheath is an important factor in its utilization.

The protective sheath, however, must also meet several demanding requirements for safety and optimal effectiveness, and satisfying these standards has typically led to relatively high costs of production. First, because the endoscope often must be inserted far inside bodily cavities, the protective sheath must be relatively long in order to completely cover all of the endoscope that is inside the body. Of course, the sheath must also be made of a material that is non-toxic and substantially inert to bodily fluids.

Because the endoscope sometimes must be bent or snaked around bones, organs or other bodily obstructions to reach the desired internal location, it is desirable for the sheath to have some degree of flexibility. At the same time, for some applications, the sidewalls of the sheath should be relatively inelastic to avoid stretching or distortions while in use, which could lead to rupture of the sheath or to damage to the body. For similar reasons, for some applications, the internal diameter of the protective sheath should be larger than the diameter of the medical instrument, but should not be larger than required to accommodate the instrument.

Up to now, it has not been possible to prepare protective sheaths of adequate lengths, having very small internal diameters, and also having the desired balance between flexibility and inelasticity of the sidewalls. All of the protective sleeves currently in use are lacking in one or more of the following desirable characteristics: (1) optically transparent, thin-walled viewing "window"; (2) thin, flexible but relatively inelastic sidewalls; (3) smooth transitions and corners; (4) reliability—i.e. no leaks; and (5) easy and inexpensive to manufacture. Specifically, it is impossible to obtain lenses with side walls of almost any length and with sidewall thicknesses less than about 0.015 inches using conventional injection molding techniques, especially if optical transparency and high strength are important. Furthermore, injection molding requires a draft or taper along the sidewalls in order to eject the finished product from the mold. Vacuum-forming or thermoforming is another technique that can be used to produce clear packaging. However, this process generally results in relatively thick walls, generously-radiused corners, and, again, substantially tapered sidewalls.

In addition, because an endoscope is an optical instrument, the protective sheath must include at least one optically transparent viewing "window" at or proximate to the closed, distal end of the sheath and in alignment with the light source and window of the endoscope. The location of the optically transparent window of the sheath will depend, in part, on whether it is to be used with an end-viewing or side-viewing endoscope. In order to maintain optical transparency and minimize visual distortions, it is desirable that the viewing window of the sheath be substantially inelastic. At the same time, as with the sheath sidewalls, some degree of flexibility in the sheath window is desirable to facilitate maneuvering the sheath and endoscope through the body and, in many cases, helping to keep the window tight against the endoscope. Whereas glass lenses are optically transparent, they are even thicker than available plastic lenses, are rigid and non-deformable, and present a potential shattering hazard, especially when made thin.

In the prior art, as discussed below, it is typical to fashion the sheath window independently of the sheath and subsequently join the two elements using adhesives or thermal bonding. Obviously, this two-step process is relatively costly and time-consuming. This two-step manufacturing process also increases the risk of sheath failure along the bonded edge. All of the prior art endoscope covers also all have thick, rigid glass or molded plastic lenses and/or sidewalls that make these devices heavy, bulky and of limited utility. They cannot be used, for example, with most small endoscopes in small body cavities, especially because the adhesive joints also add to the thickness or diameter of the final unit. Thus, present technology can produce covers for endoscopes, but these covers substantially limit the performance of the instruments, especially those with very small diameters.

Typical of the prior art in this field are U.S. Pat. Nos. 4,646,722 (Silverstein et al.) and 4,907,395 (Opie et al.). The Silverstein et al. patent teaches the use of an endoscope sheath comprising a flexible tube surrounding the elongated core of an endoscope. The flexible tube has a transparent window near its distal end positioned in front of the viewing window of the endoscope. As seen in FIG. 2 of this patent, the sheath comprises a cylindrical support body 30 having a viewing window 32 mounted at one end and a roll of elastomeric material 48 secured to support body 30.

An alternative embodiment of the Silverstein et al. sheath for use with side-viewing endoscopes is shown in FIG. 10. In this embodiment, the sheath 110 comprises an end cap 112 of relatively rigid material mounted at the end of a flexible cylindrical tube of elastomeric material 114 formed into a roll 116. The end cap 112 includes a pair of transparent windows 118, 120. Although the Silverstein et al. patent does not describe how viewing window 32 is fastened to support body 30, or how viewing windows 118, 120 are fastened to end cap 112, it is clear that these are separate and distinct components which are not formed continuously integral with the elastomeric tube. The later Opie et al. patent is essentially an improvement invention directed to a method of packaging and installing the endoscope sheaths of the Silverstein et al. patent.

U.S. Pat. Nos. 3,794,091 (Ersek et al.) and 3,809,072 (Ersek et al.) are directed to sterile sheaths for enclosing surgical illuminating lamp structures that have elongated light transmitting shafts. The sheaths in Ersek et al. are fabricated from films of flexible plastic material, such as vinyl tubing, polyethylene or polypropylene. The method of fabrications, however, is not disclosed. Ersek et al. prefer a wall thickness of between three and six mils for the required durability, rigidity and transparency. The tip end portion 20 of the sheath is described as a "generally rigid lens element" sealed to the sheath in a continuous sealing line 21 by thermal welding or adhesive bonding. Here again, it is clear that the tubular sheath portion 22 and lens element 20 are separate and distinct components which are not formed continuously integral with one another. More importantly, the lens element here is rigid and thick.

U.S. Pat. No. 4,957,112 (Yokoi et al.) describes an ultrasonic diagnostic apparatus, the distal end portion of which includes a cover 24 made of a thin, hard, polyethylene sheet that has a window portion 34 along a sidewall. At col. 4, lines 55–58, Yokoi et al. describe window 34 as being "integrally formed" with the cover 24 for permitting the passage of an ultrasonic wave from the end of the instrument. Thus, window 34 need not be optically transparent; and, cover 24 covers only a relatively small distal portion of the diagnostic instrument.

U.S. Pat. No. 4,878,485 (Adair) describes a rigid, heat sterilizable sheath S that provides an outer casing for a video endoscope. The sheath includes a viewing window 32, a flat disc positioned at the distal end positioned in the optical path of the endoscope. Window 32 is described as a "rigid" cover made of glass, sapphire or polycarbonate. Once again, it is clear that cylindrical housing 30 and window 32 are separate components, and that the lens is thick and rigid.

U.S. Pat. No. 4,819,620 (Okutsu) describes an endoscope guide pipe which is rigid and formed from a transparent material such as glass or plastic. In one embodiment shown in FIG. 6, a pair of slots in the sidewall of the guide pipe is filled with a transparent material, such as glass, to define a window section 12f.

U.S. Pat. No. 4,470,407 (Hussein) describes a flexible, elongated tube with an elastomeric balloon sealingly mounted at the distal end of the tube for enclosing an endoscope. Inside the body, the balloon can be inflated to facilitate endoscope viewing. At col. 5, line 60–col. 6, line 22, Hussein describes a process for forming the balloon in which a polished aluminum mandrel is dipped into a latex formulation that is subsequently cured. FIGS. 4 and 5 show an alternative embodiment in which a tubular stem portion of the balloon 118 surrounds and extends substantially along the length of tube 114. In either case, the tube and the balloon are separate components.

U.S. Pat. No. 4,201,199 (Smith) describes a relatively thick, rigid glass or plastic tube 10 which fits over an endoscope. The distal end of the tube in the Smith patent is provided with an enlarged, sealed bulb 12 having a radius of at least 3–4 mm to reduce optical distortion caused by a too-small radius of curvature. Although the bulb 12 is formed continuously integral with tube 10, the rounded bulb is rigid, inflexible, thick-walled, and does not yield the same degree of distortion-free optical transparency as a substantially flat window.

U.S. Pat. No. 3,162,190 (Del Gizzo) describes a tube 19, made from molded latex or similar material, through which an optical instrument is inserted. Viewing is through an inflatable balloon element 24 mounted at the distal end of the tube. Finally, U.S. Pat. No. 3,698,791 (Walchle et al.) describes a very thin, transparent microscope drape which includes a separately formed, optically transparent, distortion-free lens for viewing.

Thus, the prior art patents describe endoscope sheaths that suffer from one or more of the following disadvantages: being comprised of separate sleeve and window elements that must be bonded together, having relatively thick and/or rigid sleeve sidewalls, having rounded or elastomeric windows that result in optical distortion, and having relatively thick and rigid and/or breakable windows. These and other problems with and limitation of the prior art are overcome with the protective sheath apparatus of this invention. In particular, the method of this invention produces a sheath having a thin-walled, close-fitting sleeve with a closed, distal end comprising a thin, substantially inelastic, optically transparent window formed continuously integral with the sidewalls of the sleeve, or with a portion of the length of the sleeve, and shaped to conform with the viewing window of an endoscope.

OBJECTS OF THE INVENTION

Accordingly, it is a principal object of this invention to provide an inexpensive, disposable sheath for an optical medical instrument.

Another more specific object of this invention is to provide a disposable sheath having one or more optically transparent windows formed continuously integral with the elongated sidewalls of the sheath.

It is also an object of this invention to provide a thin-walled, close fitting, relatively inelastic, yet flexible sheath for an optical medical instrument, with an optically transparent window formed continuously integral with the sidewalls of the sheath.

Yet another object of this invention is to provide a disposable sheath, as described, that can be used by itself or by fastening it to another tubular segment.

Still a further object of this invention is to provide a method for quickly and inexpensively preparing a disposable sheath for an optical medical instrument by forming an optically transparent window continuously integral with the elongated sidewalls of the sheath.

Other objects of the invention will in part be obvious and will in part appear hereinafter. The invention accordingly comprises the method involving the several steps and the relation and order of one or more of such steps with respect to each of the others, and the apparatus possessing the construction, combination of elements, and arrangement of parts exemplified in the following detailed disclosure, and the scope of the application of which will be indicated in the claims.

SUMMARY OF THE INVENTION

The sterile, disposable sheath apparatus of this invention comprises a thin-walled, elongated, relatively inelastic sleeve of relatively small diameter having a thin, relatively inelastic, optically transparent window formed continuously integral with the sleeve. Such sleeves are produced by heating an optically transparent film of a thermoplastic material to a malleable temperature (i.e. above the glass transition temperature); inserting into the heated film a mandrel having at least one surface near its distal end shaped so as to conform with the geometry of the window of an endoscope, causing the film to stretch and form a closed-end sleeve around and conforming to the mandrel and resulting in an optically transparent window being formed adjacent the shaped surface of the mandrel; and cooling the sleeve if necessary and removing the mandrel. Because the sheaths of this invention are thin, strong, lightweight, and close-fitting, they can be utilized as protective coverings for both large and small endoscopes (ranging in diameter from about 1–25 mm) designed to access small, remote body cavities. They have the advantages of being easy and inexpensive to manufacture and having high reliability and performance because there are no seams or bonds between the sidewalls and the windows.

BRIEF DESCRIPTION OF THE DRAWINGS

In all of the drawings, as described below, it should be understood that the wall thicknesses have been greatly exaggerated relative to other elements and dimensions for purposes of illustration.

FIG. 7 is an isometric view of a disposable sheath in accordance with this invention formed integral with or over a relatively rigid disc having one or more disc apertures for receiving endoscope tubes, working channels and the like.

DETAILED DESCRIPTION OF THE DRAWINGS

In all of the drawings, as described below, it should be understood that the wall thicknesses have been greatly exaggerated relative to other elements and dimensions for purposes of illustration.

Figure 1:
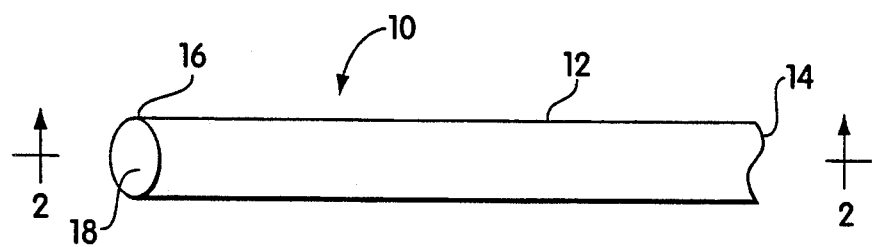
FIG. 1 is an isometric view of a disposable sheath in accordance with this invention.

FIG. 1 illustrates a disposable sheath 10 having elongated, tubular sidewalls 12, an open proximal end 14, and a closed or sealed distal end 16. End 16 comprises a substantially flat, optically transparent viewing window 18 formed continuously integral with sidewalls 12. As used herein, the term "optically transparent" means capable of transmitting visible light so that a body can be clearly seen therethrough with little or no distortion. As used herein, the term "formed continuously integral with" refers to two sections of a single element that flow substantially smoothly and continuously into one another along every interface without any discontinuous seam or edge such as that created by bonding one element to another using adhesives, thermal bonding or other techniques.

The diameter of sheath 10 may range from about 0.5–40 mm. preferably from about 3–20 mm. Smaller diameter sheaths may be selected to accommodate smaller diameter medical devices to achieve a relatively close-fitting relationship. The thickness of sidewalls 12 and end 16 should be less than 0.015 inches. For some applications, it is desirable that the sidewall thickness be less than 0.010 inches, or even less than 0.005 inches. And, for some applications, a sidewall thickness less than 0.003 inches is preferred.

For some applications, sidewalls 12 are preferably linear and of substantially uniform diameter (i.e. a cylindrical configuration); for other applications, it may be desirable to have a somewhat larger diameter proximal end with sidewalls 12 smoothly tapering to a smaller diameter distal end (i.e. a frustoconical configuration). The length of sheath 10 will vary in accordance with the length of the medical instrument to be covered and the remoteness of the body cavity to be viewed, but sheath lengths ranging from about one-quarter inch to several feet are within the scope of this invention. The ratio of the diameter of the sheath to its length may range from about 1:1 to 1:100. Only the method of this invention makes possible the manufacture of very thin-walled (less than about 0.010 inches) integrally formed sheaths of very small diameters and relatively long lengths.

As seen in FIG. 1, end 16 of sheath 10 comprises a substantially flat, optically transparent viewing window 18 formed continuously integral with sidewalls 12. In other words, no adhesive, thermal bonding or other sealing process is required to fasten window 18 to sidewalls 12. Like sidewalls 12, window 18 is very thin, typically having a thickness less than 0.015 inches. Even more important than the thickness of the window is the thickness of the sidewalls 12 because it is the thickness of the sidewalls that limits the overall diameter of the covered endoscope unit. Furthermore, as noted previously, if a separate window has to be bonded to the sidewalls, the bond itself adds undesirable thickness to the diameter of the unit at the bonding point thereby limiting the utility of the entire instrument. The present invention facilitates minimizing the overall diameter of a covered endoscope unit by combining very thin sheath sidewalls with an integral window that requires no bonding.

Figure 2:
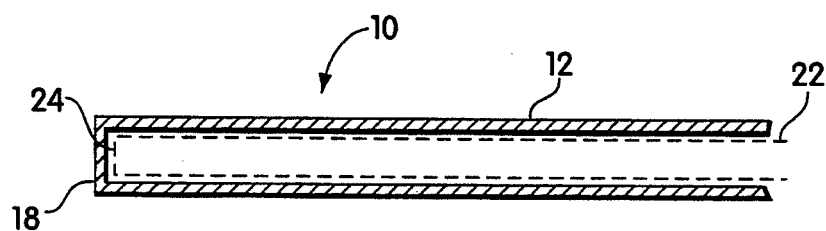
FIG. 2 is a side elevational view in cross-section along the line 2—2 of the sheath of FIG. 1 with an enclosed medical instrument shown in dotted outline.

Sheath 10 of FIG. 1 is designed as a protective covering for an end-view endoscope or similar optical medical instrument. Thus, the plane of window 18 is substantially normal to the axis of sheath 10. For example, FIG. 2 shows a side elevational view in cross-section along the line 2—2 of the sheath of FIG. 1 with an end-view endoscope 22, having a lens and/or light source 24 at the distal end thereof, shown in dotted outline inside sheath 10. Lens 24 of endoscope 22 is normal to the axis of the instrument and is positioned in close proximity to and in axial alignment with viewing window 18.

Figure 3:
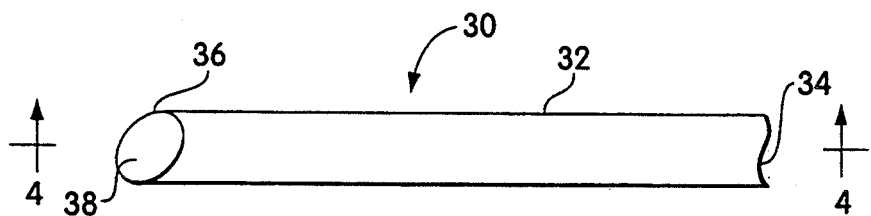
FIG. 3 is an isometric view of another embodiment of a disposable sheath in accordance with this invention.
Figure 4:
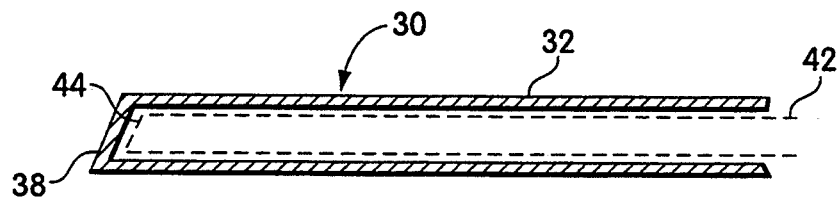
FIG. 4 is a side elevational view in cross-section along the line 4—4 of the sheath of FIG. 2 with an enclosed medical instrument shown in dotted outline.

FIG. 3 illustrates an alternative embodiment of this invention. In this embodiment, sheath 30 has elongated tubular sidewalls 32, an open proximal end 34, and an angled or sloping closed distal end 36. End 36 comprises a substantially flat, optically clear viewing window 38 formed continuously integral with sidewalls 32. Sheath 30 of FIG. 3 is designed as a protective covering for an endoscope or similar optical medical instrument 42 having a slanted lens 44, as seen in FIG. 4. Similar to the embodiment shown in FIG. 2, the angled or sloping end 36 of sheath 30 facilitates positioning lens 44 of endoscope 42 adjacent to and in alignment with viewing window 38.

End 36 of sheath 30 can be made sloping at virtually any angle required to accommodate the geometry of the lens of the medical instrument. As discussed below, sheaths having other distal end geometries, e.g. curved or parabolic, can also be prepared in accordance with this invention to correspond with similarly shaped endoscope lenses.

Figure 5:
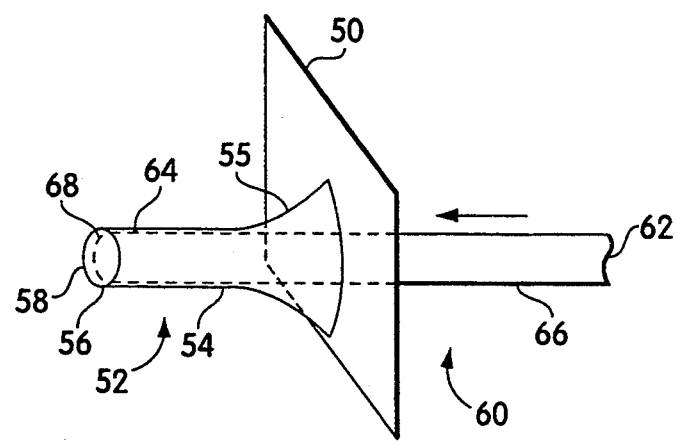
FIG. 5 is an isometric view of a heated thermoplastic film being stretched by a mandrel to form a protective sheath in accordance with this invention.

FIG. 5 illustrates one embodiment of the method for preparing the protective sheaths of this invention. A sheet or film 50 of an optically transparent polymeric material is heated to a point where its viscosity is substantially reduced thus rendering it malleable. A male forming tool or mandrel 60 having a proximal end 62, a distal end 64, and sidewalls 66, is thrust into heated film 50 causing it to stretch and conform to the geometry of the mandrel thereby forming a closed end sleeve 52 having sidewalls 54, a flange or collar 55 at its proximal end, and a distal end 56. As seen in FIG. 5, distal end 64 of mandrel 60 comprises a substantially flat face or surface 68 that is substantially normal to the axis of mandrel 60. As a result, the distal end 56 of sleeve 52 is formed having a substantially flat, optically transparent window 58 continuously integral with sidewalls 54 and substantially normal to the axis of sleeve 52 (i.e. a sheath similar to that of FIG. 1). For some applications, as described hereinafter, mandrel 60, at a suitable location along its length, may include a collar mold (not shown) of a generally bell-like shape. The effect of the collar mold is to cause flange 55 of sleeve 52 to conform to the shape of the collar mold. Such a molded flange section is designed to protect portions of the instruments outside the body from contamination.

By varying the geometry of mandrel 60, sheaths having a wide variety of shapes and sizes can be formed using the method of this invention. For example, instead of the flat, normal face 68 of mandrel 60 in FIG. 5, a mandrel having a slanted or angled face could be used to produce sheaths similar to that of FIG. 3. A mandrel with a substantially flat face along sidewalls 66 proximate to distal end 64 could be used to produce sheaths having optically transparent windows along their sidewalls to accommodate side-view endoscopes. A mandrel with a curved or parabolic distal end could be used to produce sheaths having comparable geometry.

As previously discussed, the forming process may also include integrally forming a molded collar having a diameter or cross-section larger than the rest of the sleeve at the open, proximal end of the sheath. Such a collar can be useful in covering the portion of the medical instrument located outside but adjacent to the body or in attaching a clamp to hold the sheath on to the scope. Instead of integrally forming the molded collar section as discussed above, conventional plastic processing techniques, such as thermoforming or injection molding, can also be used.

Instead of using a mandrel with tubular sidewalls 66 to produce sheaths with tubular sidewalls, the mandrel can be made with flat sidewalls to produce sheaths having various polyhedral cross-sectional configurations, e.g. triangular (3 flat sides) or rectangular (4 flat sides). Instead of using a mandrel with substantially cylindrical sidewalls 66, the mandrel can be made in a frustoconical configuration to produce tubular sheaths with a smooth inward taper from the proximal to the distal end.

Still another variation of this invention is to use a mandrel having a hollow end or hollow core. A hollow end forming tool would allow air to enter the interior of the sheath as the tool is withdrawn to prevent collapse of the sheath. Alternatively, a hollow core or internal channel in the mandrel could be used to supply air or another fluid (gas or liquid) to blow the formed sheath off of the tool. In a related variation of this invention, a double-walled cavity or channel inside the mandrel can be used, where desirable, to circulate a heat transfer fluid inside the mandrel for selectively heating or cooling the mandrel at various stages of the process of this invention. Other well known methods may also be used for selectively heating or cooling the mandrel.

For some applications, it may be desirable for at least a portion of the sheath sidewall 54 to have a ribbed, accordian-like structure. Somewhat analogous to drinking straws with an accordian-like section, this configuration enhances the flexibility of the sheath and facilitates installation of the combined unit into the body and articulation of the endoscope once in position. Such an accordian-like structure is readily achieved by axially compressing or sandwiching all or a selected portion of the formed sheath.

In yet another embodiment of this invention, sheaths with multi-layer sidewalls can be prepared by the methods described herein. Such multi-layer sidewalls can be utilized to provide enhanced reliability or durability, or, by using different materials for the different layers, to custom-tailor the properties of the sheath to a particular requirement. For example, it may be desirable to choose an inner sidewall of a very high strength polymer in combination with an outer sidewall of a very slippery polymer to facilitate insertion of the covered endoscope into the body. Such multi-layer sidewalls, and multi-layer molded collar sections if desired, can be formed by thrusting the mandrel 60 into a first heated film and, without removing the first-formed sheath, subsequently thrusting the sheathed mandrel into a second, third, etc. heated film to form second, third, etc. layers. For optical clarity, it may be desirable to cut off or otherwise remove all but one lens layer. Alternatively, a thin-walled thermoplastic or heat-shrinkable tube may be placed on the forming mandrel prior to thrusting the mandrel into a first heated film to form a two-layer sidewall of enhanced durability.

Figure 6:
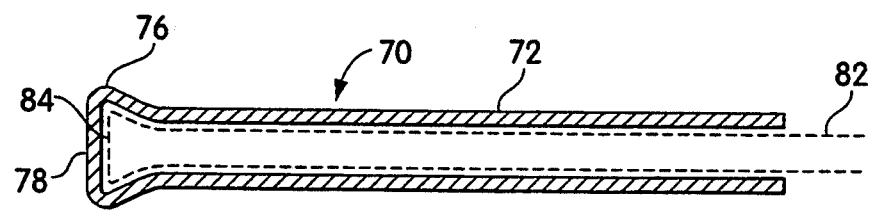
FIG. 6 is a side elevational view in cross-section of still another embodiment of a disposable sheath in accordance with this invention.

FIG. 6 illustrates still another embodiment of this invention in which the window end 76 of sheath 70 is flared outward such that the outer diameter of the window 78 is slightly larger than the diameter of the rest of the sheath. Thus, for example, the outer diameter of window 78 may be about 0.001–0.015 inches greater than the outer diameter of sidewall section 72. Flared window sheaths in accordance with this embodiment of the invention can be prepared similar to the methods described above in connection with FIGS. 2, 4 and 5, except that the mandrel or forming tool 82 will have a collapsible core or split ring construction at its distal end 84 to facilitate withdrawing the tool from the flared window sheath.

Figure 7:
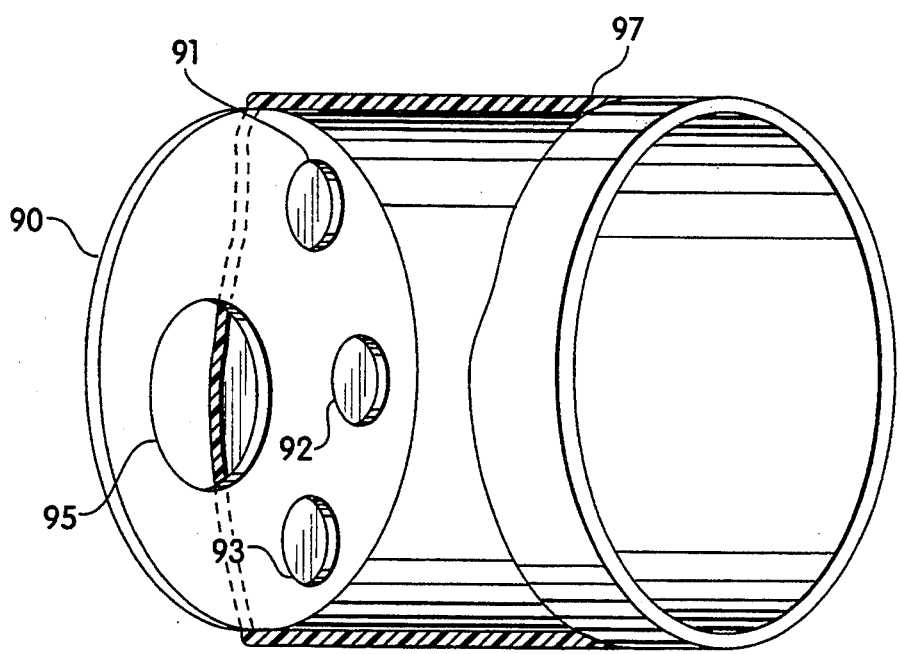

Yet another embodiment of this invention is illustrated in FIG. 7 which shows a sheath prepared in accordance with this invention formed over a relatively rigid, apertured plastic disc 90. Disc 90 comprises one or a plurality of disc apertures 91, 92 and 93, sized and shaped so as to mate with one or more working channels or elements of the endoscope intended to be covered by sheath 97. Disc 90 also comprises a window aperture 95 sized and shaped to mate with the viewing lens of the endoscope and to position that lens in alignment with the viewing window at the distal end of sheath 97.

Disc 90 provides alignment of and stability to the various elements of the medical instrument being covered by sheath 97, for example by providing a rigid body for attaching the tubes projecting from the distal end of an endoscope. Thus, disc apertures 91 and 93 can communicate with working channels in the endoscope (not shown) while aperture disc 92 accommodates a fiber optic light coming through the endoscope. Also, holes may be cut in the portion of sheath 97 adjacent the various disc apertures to accommodate tubes or working channels intended to extend beyond the distal end of sheath 97.

Disc 90 can be prepared in virtually any desired size and shape through conventional injection molding or die cutting techniques. Disc 90 can be prepared such that apertures 91, 92, 93 and 95 are formed simultaneously with the disc or, alternatively, the apertures can be cut or punched from a preformed disc. Sheath 97, having thin sidewalls and a thin, optically transparent window in accordance with this invention, can be formed over a prefabricated disc 90 that has been placed at the end of the forming mandrel. Tubing or other components can be attached to the disc either before or after sheath formation.

A variety of orientable and non-orientable elastoplastic polymeric materials can be used as the optically transparent starting film for producing the sheaths of this invention. Preferred starting materials include thin films of clear thermoplastics including thermoplastic polyesters such as PET, and PETG (a glycol-modified polyethylene terephthalate), PVC, acrylic and polycarbonate. These polymers provide an optimum combination of properties for producing long, small-diameter, thin-walled sheaths of high strength, flexible yet substantially inelastic sidewalls, and flexible, inelastic, optically transparent windows.

For some specialized applications, instead of starting with a film of optically clear polymer, it may be desirable to choose a pigmented or tinted or coated polymeric film, for example a film coated with an antireflective coating. The resulting sheaths would have windows capable of filtering specific wavelengths of light. For other applications, it may be desirable to choose a polymeric film that is transparent to lasers.

Figure 8:
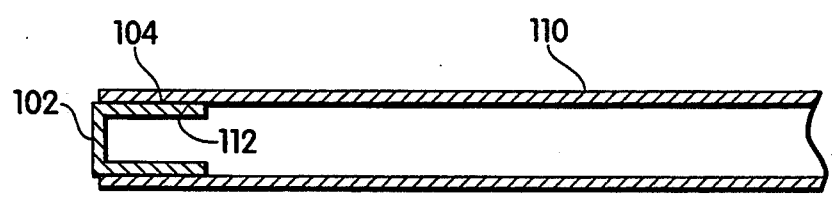
FIG. 8 is a side elevational view in cross-section of a first embodiment wherein a disposable sheath in accordance with this invention is utilized as an end sleeve or cap in conjunction with tubing.
Figure 9:
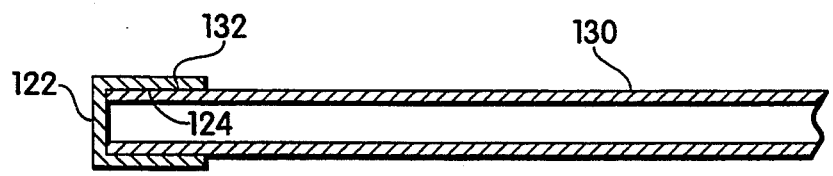
FIG. 9 is a side elevational view in cross-section of a second embodiment wherein a sheath in accordance with this invention is utilized as an end sleeve or cap.

For some applications, it may be desirable to utilize the protective sheaths of this invention as caps or end sleeves attached to longer pieces of hollow tubing as illustrated in FIGS. 8 and 9. For such applications, the components can be joined using various common techniques, for example solvent bonding, adhesive bonding, heat bonding, ultrasonic welding, etc. Although the general concept of using an end cap mounted at the end of flexible tubing is described in U.S. Pat. No. 4,646,722 (Silverstein et al.), the sidewalls of the Siverstein et al. end caps are thick and the viewing windows are separately bonded to those sidewalls thereby further increasing the overall diameter of the end cap-sleeve combination. By contrast, when the protective sheaths of this invention are used as end sleeves, the thin side wall and integral window construction is preserved. Indeed, the end sleeves of this invention can be advantageously used in place of the end caps described in the Silverstein et al. patent as well as other prior art end caps.

For example, in FIG. 8, a sheath 102 is prepared in accordance with this invention such that sheath 102 has an outer diameter approximately equal to or less than the inner diameter of elongated tubing 110 so that sheath 102 fits concentrically inside tubing 110. Outer sidewall 104 of sheath 102 is bonded by appropriate means to one end of the inner sidewall 112 of tubing 110 to form the complete protective sheath apparatus.

Correspondingly, in FIG. 9, a sheath 122 is prepared in accordance with this invention such that sheath 122 has an inner diameter approximately equal to or greater than the outer diameter of elongated tubing 130 so that sheath 122 fits concentrically over one end of tubing 130. Inner sidewall 124 of sheath 122 is bonded by appropriate means to the outer sidewall 132 of tubing 130 to form the complete protective sheath apparatus.

Alternatively, a tube or series of tubes may be placed over or inside the forming tool and the window, as described previously, can be formed integrally over the tube, eliminating a secondary bonding step. This may be desirable for example when a very thin lens and a thick or stiff sidewall is wanted. Other types of reinforcement may be used, for example the sleeve could be formed over a spring or reinforcing wires or other shaped products.

For some applications, it may be desirable to fill the space between the exterior of the medical instrument and the interior of the protective sheath with an image-enhancing or coupling fluid, for example water or glycerine. In still another embodiment, there are certain types of endoscopes that have working channels for sampling fluids, flushing, drainage etc. It is possible to thermally seal these tubes to the transparent lens by carefully positioning the tubes so that the ends of the tubes contact the soft hot film and fuse to the film during forming, or, alternatively, they can be attached later.

The protective sheaths of this invention can also be used for other purposes beyond a sterile cover. For example, in arthroscopic surgery such as knee surgery high speed sharp cutters are used to shave away bones. In order to get the best view, these scopes are placed very close to the cutting area. This often results in accidental damage to the optics of the scope. This often occurs in teaching hospitals where student doctors practice these surgical techniques. Use of a protective sleeve in accordance with this invention can reduce the damage to these scopes, saving thousands of dollars in repair costs for a single scope.

Since other changes may be made in the above-described apparatus and process without departing from the scope of the invention herein involved, it is intended that all matter contained in the above description shall be interpreted in an illustrative and not in a limiting sense.

Having described the invention, what is claimed is:

1. Sheath apparatus for covering a medical instrument used for internal body applications, said apparatus comprising a thin-walled polymeric sleeve having at least one open end and at least one closed end, wherein said closed end comprises a thin, substantially inelastic, optically transparent window formed continuously integral with said sleeve.

2. The apparatus of claim 1 wherein the walls of said sleeve have a thickness less than 0.010 inches.

3. The apparatus of claim 1 wherein the walls of said sleeve have a thickness less than 0.005 inches.

4. The apparatus of claim 1 wherein the walls of said sleeve have a thickness less than 0.003 inches.

5. The apparatus of claim 1 wherein said sleeve has a substantially uniform cross-sectional configuration along its length.

6. The apparatus of claim 1 wherein said sleeve is inwardly tapered from said open end toward said closed end.

7. The apparatus of claim 1 wherein the ratio of the diameter of said sleeve to its length ranges from about 1:1 to 1:100.

8. The apparatus of claim 1 wherein said polymeric sleeve and window consist essentially of a polymer selected from the group consisting of thermoplastic polyesters, PVC, acrylic and polycarbonate.

9. The apparatus of claim 8 wherein said polymer is a thermoplastic polyester selected from the group consisting of PET and PETG.

10. The apparatus of claim 8 wherein said polymer is optically clear.

11. The apparatus of claim 8 wherein said polymer is pigmented, tinted or coated.

12. The apparatus of claim 8 wherein said polymer is transparent to lasers.

13. The apparatus of claim 1 wherein said open end of said sleeve comprises an integrally formed collar having a cross-section larger than that of the rest of said sleeve.

14. The apparatus of claim 1 further wherein at least a portion of the walls of said sleeve comprise a ribbed, accordian-like structure.

15. Apparatus according to claim 1 wherein said sheath comprises a plurality of layers, each said layer comprising a thin-walled polymeric sleeve and an optically transparent window formed continuously integral with said sleeve.

16. Apparatus according to claim 15 further wherein all but one of said optically transparent windows have been removed.

17. Apparatus according to claim 1 wherein said window has an outer diameter greater than the outer diameter of said sleeve.

18. Apparatus according to claim 1 wherein the outer diameter of said window is about 0.001–0.015 inches greater than the outer diameter of said sleeve.

19. Sheath apparatus for covering a medical instrument used for internal body applications, said apparatus comprising hollow tubing having an open proximal end and, fastened at the distal end thereof, a thin-walled polymeric sleeve having a closed distal end wherein said distal end comprises a thin, substantially inelastic, optically transparent window formed continuously integral with said sleeve.

20. Apparatus according to claim 19 wherein the walls of said sleeve have a thickness less than 0.010 inches.

21. Apparatus according to claim 19 wherein the walls of said sleeve have a thickness less than 0.005 inches.

22. Apparatus according to claim 19 wherein the walls of said sleeve have a thickness less than 0.003 inches.

23. Apparatus according to claim 19 wherein said window has an outer diameter greater than the outer diameter of said sleeve.

24. Apparatus according to claim 19 wherein said window is substantially flat and lies in a plane substantially normal to the longitudinal axis of said sleeve.

25. Apparatus according to claim 19 wherein said window is substantially flat and lies in a plane which intersects the longitudinal axis of said sleeve at an acute angle.

26. Apparatus according to claim 19 wherein said window is substantially flat and lies in a plane substantially parallel to the longitudinal axis of said sleeve so as to align said window with an optical viewing window of a side-viewing type endoscope.

27. Medical apparatus for internal body applications comprising in combination an optical instrument and a protective covering therefor, said protective covering comprising a thin-walled, polymeric sleeve closely fit to the exterior distal end of said optical instrument, said sleeve comprising an open end and a closed end, said closed end comprising a thin, substantially inelastic, optically transparent window formed continuously integral with said sleeve.

28. The apparatus of claim 27 wherein said sleeve comprises a single, integrally formed unit that covers all of the optical instrument that is located inside the body when the instrument is in use.

29. The apparatus of claim 27 further including an image-enhancing fluid located between the exterior of the distal end of said optical instrument and the interior of said sleeve.

30. The apparatus of claim 27 wherein the walls of said sleeve have a thickness less than 0.010 inches.

31. The apparatus of claim 27 wherein the walls of said sleeve have a thickness less than 0.005 inches.

32. The apparatus of claim 27 wherein the walls of said sleeve have a thickness less than 0.003 inches.

33. The apparatus of claim 27 wherein said polymer sleeve and window consist essentially of a polymer selected from the group consisting of thermoplastic polyesters, PVC, acrylic and polycarbonate.

34. The apparatus of claim 33 wherein said polymer is a thermoplastic polyester selected from the group consisting of PET and PETG.

35. The apparatus of claim 27 wherein said open end of said sleeve comprises an integrally formed collar for covering the portion of the optical instrument located outside but adjacent to the body when the instrument is in use.

36. Apparatus according to claim 27 further wherein at least a portion of the walls of said sleeve comprise a ribbed, accordian-like structure.

37. Apparatus according to claim 27 wherein said protective covering comprises a plurality of layers, each said layer comprising a thin-walled polymeric sleeve and an optically transparent window formed continuously integral with said sleeve.

38. Apparatus according to claim 32 further wherein all but one of said optically transparent windows have been removed.

39. Apparatus according to claim 27 further comprising hollow tubing having an open proximal end and fastened at the distal end thereof to the open end of said polymeric sleeve.

40. Apparatus according to claim 39 wherein the walls of said polymeric sleeve have a thickness less than 0.010 inches.

41. Apparatus according to claim 39 wherein the walls of said polymeric sleeve have a thickness less than 0.005 inches.

42. Apparatus according to claim 39 wherein the walls of said polymeric sleeve have a thickness less than 0.003 inches.

43. Apparatus according to claim 27 wherein said window has an outer diameter greater than the outer diameter of said sleeve.

44. Apparatus according to claim 24 wherein said optical instrument comprises a viewing portion at its distal end, and further wherein said window has a geometry comparable to that of said viewing portion so as to minimize optical distortion.

45. Apparatus according to claim 44 wherein said viewing portion is substantially flat and lies in plane substantially normal to the longitudinal axis of the optical instrument, and further wherein said window is also substantially flat and lies in a plane substantially normal to the longitudinal axis of said sleeve.

46. Apparatus according to claim 44 wherein said viewing portion is substantially flat and lies in a plane which intersects the longitudinal axis of the optical instrument at an acute angle, and further wherein said window is also substantially flat and lies in a plane which intersects the longitudinal axis of said sleeve at substantially the same acute angle as said viewing portion.

47. Apparatus according to claim 44 wherein said viewing portion is substantially flat and lies in a plane substantially parallel to the longitudinal axis of the optical instrument, and further wherein said window is also substantially flat and lies in a plane substantially parallel to the longitudinal axis of said sleeve so as to align said window with an optical viewing window of a side-viewing type endoscope.

48. Apparatus according to claim 44 wherein said viewing portion is curved, and further wherein said window is substantially concentric with respect to said curved viewing portion.

49. An elongated, tubular sleeve for covering an optical medical instrument used for internal body applications, said sleeve comprising at a distal end thereof a thin, substantially inelastic, optically transparent window formed continuously integral with the side wall of said sleeve by the process of: heating an optically transparent film of a polymeric material to a malleable temperature; inserting into said heated film a mandrel having at least one shaped surface near its distal end, said surface being shaped so as to conform with the geometry of the optical portion of said medical instrument, causing the film to stretch and form a closed-end sleeve around and conforming to said mandrel, said window being formed adjacent said shaped surface of said mandrel; and removing the mandrel.

50. Sleeve according to claim 49 wherein said shaped surface has an outer diameter greater than the outer diameter of the rest of said mandrel so as to form a sleeve having a flared window at its distal end.

51. Sleeve according to claim 49 wherein said optical portion of said medical instrument is substantially flat and lies in a plane substantially normal to the longitudinal axis of the medical instrument, and further wherein said window is also substantially flat and lies in a plane substantially normal to the longitudinal axis of said sleeve.

52. Sleeve according to claim 49 wherein said optical portion of said medical instrument is substantially flat and lies in a plane which intersects the longitudinal axis of the medical instrument at an acute angle, and further wherein said window is also substantially flat and lies in a plane which intersects the longitudinal axis of said sleeve at substantially the same acute angle as said optical portion.

53. Sleeve according to claim 49 wherein said optical portion of said medical instrument is substantially flat and lies in a plane substantially parallel to the longitudinal axis of the medical instrument, and further wherein said window is also substantially flat and lies in a plane substantially parallel to the longitudinal axis of said sleeve so as to align said window with an optical viewing window of a side-viewing type endoscope.

54. Sleeve according to claim 49 wherein said optical portion of said medical instrument is curved, and further wherein said window is substantially concentric with respect to said curved optical portion.

55. Sheath apparatus for covering a medical instrument used for internal body applications, said apparatus comprising a thin-walled polymeric sleeve having a least one open end and at least one closed end, wherein said closed end comprises a thin, substantially inelastic, optically transparent window formed continuously integral with said sleeve, and a relatively rigid, apertured disc inside said sleeve and adjacent said window.

56. Sheath apparatus for covering a medical instrument used for internal body applications, said apparatus comprising hollow tubing having an open proximal end and, fastened at the distal end thereof, a thin-walled polymeric sleeve having a closed distal end wherein said distal end comprises a thin, substantially inelastic, optically transparent window formed continuously integral with said sleeve, and relatively rigid, apertured disc inside said sleeve and adjacent said window.

57. Apparatus according to claim 56 wherein said disc is integrally formed with said sleeve.

58. Medical apparatus for internal body applications comprising in combination an optical instrument and a protective covering therefor, said protective covering comprising a thin-walled, polymeric sleeve closely fit to the exterior distal end of said optical instrument, said sleeve comprising an open end and a closed end, said closed end comprising a thin, substantially inelastic, optically transparent window formed continuously integral with said sleeve, and a relatively rigid, apertured disc inside said sleeve and adjacent said window.

59. Apparatus according to claim 58 wherein said disc is integrally formed with said sleeve.

60. Sheath apparatus for covering a medical instrument used for internal body applications, said apparatus comprising a thin-walled polymeric sleeve having a least one open end and at least one closed end, wherein said closed end comprises a thin, substantially inelastic, optically transparent window formed continuously integral with said sleeve such that said window and said sleeve flow substantially smoothly and continuously into one another along every interface without any discontinuous seam or edge.

61. Sheath apparatus for covering a medical instrument used for internal body applications, said apparatus comprising hollow tubing having an open proximal end and, fastened at the distal end thereof, a thin-walled polymeric sleeve having a closed distal end wherein said distal end comprises a thin, substantially inelastic, optically transparent window formed continuously integral with said sleeve such that said window and said sleeve flow substantially smoothly and continuously into one another along every interface without any discontinuous seam or edge.

62. Medical apparatus for internal body applications comprising in combination an optical instrument and a protective covering therefor, said protective covering comprising a thin-walled, polymeric sleeve closely fit to the exterior distal end of said optical instrument, said sleeve comprising an open end and a closed end, said closed end comprising a thin, substantially inelastic, optically transparent window formed continuously integral with said sleeve such that said window and said sleeve flow substantially smoothly and continuously into one another along every interface without any discontinuous seam or edge.

63. An elongated, tubular sleeve for covering an optical medical instrument used for internal body applications, said sleeve comprising at a distal end thereof a thin, substantially inelastic, optically transparent window formed continuously integral with the side wall of said sleeve such that said window and said sleeve flow substantially smoothly and continuously into one another along every interface without any discontinuous seam or edge by the process of: heating an optically transparent film of a polymeric material to a malleable temperature; inserting into said heated film a mandrel having at least one shaped surface near its distal end, said surface being shaped so as to conform with the geometry of the optical portion of said medical instrument, causing the film to stretch and form a closed-end sleeve around and conforming to said mandrel, said window being formed adjacent said shaped surface of said mandrel; and removing the mandrel.

64. Apparatus according to claim 1 wherein said window is substantially flat and lies in a plane which intersects the longitudinal axis of said sleeve at an acute angle.

65. Apparatus according to claim 1 wherein said window is substantially flat and lies in a plane substantially parallel to the longitudinal axis of said sleeve.

66. Apparatus according to claim 19 wherein said window is substantially flat and lies in a plane substantially normal to the longitudinal axis of said sleeve.

* * * * *

UNITED STATES PATENT AND TRADEMARK OFFICE
CERTIFICATE OF CORRECTION

PATENT NO. : 5,337,734
DATED : August 16, 1994
INVENTOR(S) : Mark A. Saab

It is certified that error appears in the above-indentified patent and that said Letters Patent is hereby corrected as shown below:

Col. 13, line 4 - delete "24" and substitute therefor — 27 —.

Col. 16, line 14 - after "said sleeve" insert — so as to align said window with an optical viewing window of a side-viewing type endoscope —.

Col. 16, line 15 - delete "19" and substitute therefor — 1 —.

Col. 16, line 18 - add the following claim:

— 67. Apparatus according to claim 55 wherein said disc is integrally formed with said sleeve. —

Signed and Sealed this

Twenty-first Day of May, 1996

Attest:

BRUCE LEHMAN

Attesting Officer    Commissioner of Patents and Trademarks